United States Patent [19]

Breuer et al.

[11] 4,063,019
[45] Dec. 13, 1977

[54] [[[(2,4-DIOXO-1-IMIDAZOLIDINYL-)AMINO]CARBONYL]AMINO]-ACETYL-CEPHALOSPORIN DERIVATIVES

[75] Inventors: Hermann Breuer; Uwe D. Treuner, both of Regensburg, Germany

[73] Assignee: E. R. Squibb & Sons, Inc., Princeton, N.J.

[21] Appl. No.: 671,788

[22] Filed: Mar. 30, 1976

[51] Int. Cl.² .......................................... C07D 501/36
[52] U.S. Cl. ................................... 544/27; 424/246; 544/21; 260/332.2 A; 548/311; 548/309
[58] Field of Search ................................ 260/243 C

[56] References Cited
U.S. PATENT DOCUMENTS 3,708,479  1/1973  Welch et al. ............... 260/243 C
3,925,368  12/1975  Cooper et al. .............. 260/243 C
3,956,288  5/1976  Bambury .................... 260/243 C Primary Examiner—Nicholas S. Rizzo
Assistant Examiner—David E. Wheeler
Attorney, Agent, or Firm—Lawrence S. Levinson; Merle J. Smith

[57] ABSTRACT

[[[(2,4-Dioxo-1-imidazolidinyl)amino]carbonyl]amino]-acetylcephalosporin derivatives having the formula

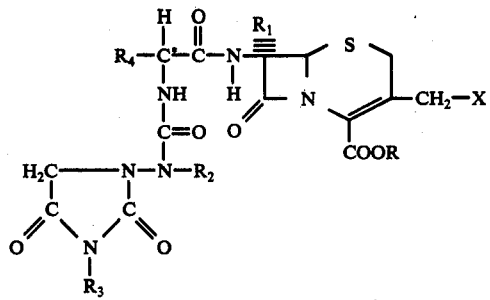

wherein R is hydrogen, lower alkyl, phenyl-lower alkyl, diphenyl-lower alkyl, tri(lower alkyl)silyl, trihaloethyl, a salt forming ion, or the group

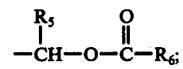

$R_1$ is hydrogen or methoxy; $R_2$, $R_3$ and $R_5$ each is hydrogen or lower alkyl; $R_4$ is hydrogen, lower alkyl, cyclo-lower alkyl, cyclo-lower alkenyl, cyclo-lower alkadienyl, phenyl, phenyl-lower alkyl, substituted phenyl, substituted phenyl-lower alkyl, or certain heterocyclic groups; $R_6$ is lower alkyl; and X is hydrogen, lower alkanoyloxy,

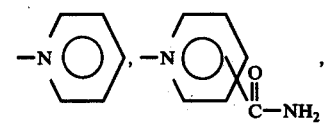

or certain heterothio groups; are useful as antibacterial agents.

12 Claims, No Drawings

[[[(2,4-DIOXO-1-IMIDAZOLIDINYL)AMINO]CARBONYL]AMINO]-ACETYLCEPHALOSPORIN DERIVATIVES

BACKGROUND OF THE INVENTION

Cephalosporins having a ureido acyl side chain are disclosed in U.S. Pat. Nos. 3,673,183; 3,708,479, 3,833,568 and 3,860,591. Cephalosporins having various acyl side chains and a 7α-methoxy substituent are taught in various U.S. Pat. Nos. including 3,775,410; 3,780,031; 3,780,033; 3,780,034, 3,780,037; 3,843,641, etc.

Cephalosporins having an acylureido acyl side chain are disclosed in U.S. Pat. Nos. 3,687,949 and 3,925,368 and German Offenlegungsschrift Nos. 2,513,954 and 2,514,019.

SUMMARY OF THE INVENTION

This invention relates to new [[[(2,4-dioxo-1-imidazolidinyl)amino]carbonyl]amino]acetylcephalosporin derivatives having the formula

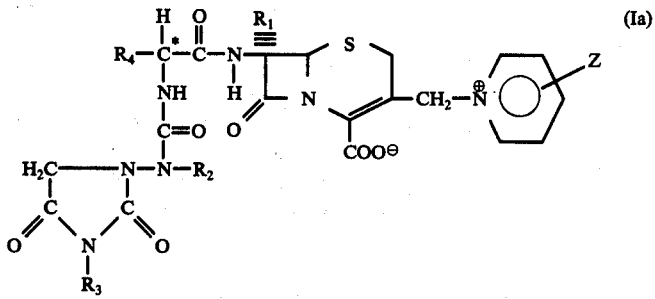

R represents hydrogen, lower alkyl, phenyl-lower alkyl, diphenyl-lower alkyl, tri(lower alkyl)silyl, trihaloethyl, a salt forming ion, or the group

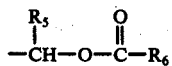

wherein $R_5$ is hydrogen or lower alkyl and $R_6$ is lower alkyl.

$R_1$ represents hydrogen or methoxy. The $R_1$ substituent is in the α-configuration as indicated by the broken lines (≡).

$R_2$ and $R_3$ each represents hydrogen or lower alkyl.

$R_4$ represents hydrogen, lower alkyl, cyclo-lower alkyl, cyclo-lower alkenyl, cyclo-lower alkadienyl, phenyl, phenyl-lower alkyl, substituted phenyl, substituted phenyl-lower alkyl, or certain heterocyclic groups.

X represents hydrogen, lower alkanoyloxy, certain heterothio groups,

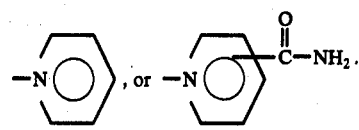

When X is pyridinium or carbamoyl substituted pyridinium, the compounds can be structurally represented as having the formula wherein Z is hydrogen or carbamoyl.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons and especially 1 or 2 carbons. Examples of the type of groups contemplated are methyl, ethyl, propyl, isopropyl, butyl, t-butyl, etc. The lower alkoxy groups (referred to below) include such lower alkyl groups attached to an oxygen, e.g., methoxy, ethoxy, propoxy, etc. The phenyl-lower alkyl and diphenyl-lower alkyl groups include such lower alkyl groups attached to a phenyl with the same preferred groups as above but especially benzyl, phenethyl and diphenyl methyl.

The cyclo-lower alkyl groups are alicyclic groups having 3 to 7 carbons in the ring, i.e., cyclopropyl, cyclobutyl, cyclopentyl, cyclohexyl and cycloheptyl. The cyclo-lower alkenyl groups represent rings having 4 to 7 carbons with one double bond, i.e., cyclobutenyl, cyclopentenyl, cyclohexenyl, etc. The term cycloalkadienyl represents a ring having 6 or 7 carbons with two double bonds located at various positions such as 1,4-cyclohexadienyl which is especially preferred. The $C_5$-$C_6$ alicyclics are preferred.

The substituted phenyl and substituted phenyl-lower alkyl groups include those having one or two substituents on the phenyl ring, e.g., halogen (preferably chlorine or bromine), lower alkyl (preferably $C_1$-$C_4$ and especially methyl or ethyl), lower alkoxy (preferably $C_1$-$C_4$ and especially methoxy or ethoxy), or hydroxy, e.g., 2-, 3- or 4-chlorophenyl, 2-, 3- or 4-bromobenzyl, 2-, 3- or 4-hydroxyphenyl, 3,5-dichlorophenyl, 2-, 3- or 4-methylphenyl, 2-, 3- or 4-ethoxyphenyl, etc. The 4-monosubstituted phenyl groups are preferred.

The salt forming ions represented by R are metal ions, e.g., aluminum, alkali metal ions such as sodium or potassium, alkaline earth metal ions such as calcium or magnesium, or amine salt ions, of which a number are known for this purpose, for example, phenyl-lower alkylamines, such as dibenzylamine, N,N-dibenzylethylenediamine, lower alkylamines such as methylamine, ethylamine, tri(lower alkyl) amine such as triethylamine, and N-lower alkylpiperidines such as N-ethylpiperidine. Sodium and potassium are the preferred salt forming ions.

The halogens are the four common halogens, of which chlorine and bromine are preferred. In the case of the trihaloethyl group represented by R, 2,2,2-trichloroethyl is preferred.

Trimethylsilyl is the preferred tri(lower alkyl)-silyl group.

The heterocyclic groups represented by $R_4$ are 2-thienyl, 3-thienyl, 2-furyl, 3-furyl, 2-pyridyl, 3-pyridyl or 4-pyridyl. Also included within the meaning of $R_4$ are such heterocyclics having as a substituent $R_9$ which is halogen (preferably chlorine or bromine) or lower alkyl (preferably $C_1$-$C_4$ and especially methyl or ethyl) substituent, i.e., 2-(4-chlorothienyl), 3-(4-methylthienyl), etc.

The lower alkanoyloxy groups are the acyl groups of the lower fatty acids having the formula

lower alkyl, preferably wherein lower alkyl is of 1 to 4 carbons, especially methyl.

The heterothio groups represented by X are

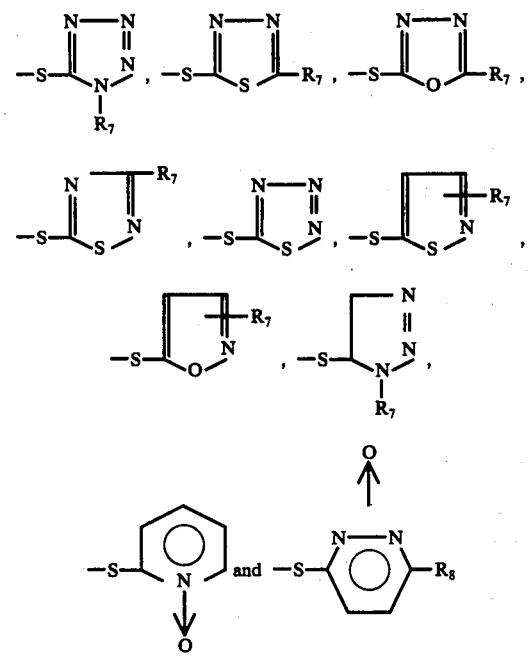

wherein $R_7$ is hydrogen or lower alkyl (preferably $C_1$-$C_4$ and especially methyl or ethyl) and $R_8$ is hydrogen, lower alkyl (preferably $C_1$-$C_4$ and especially methyl or ethyl), methoxy, hydroxy or halogen (preferably chlorine). Especially preferred are the tetrazole group above wherein $R_7$ is methyl, the 1,3,4-thiadiazole group above wherein $R_7$ is methyl and the 4-carbamylpyridinium group.

The compounds of formula I wherein $R_1$ is hydrogen can be prepared by several methods. For example, an α-amino intermediate of the formula

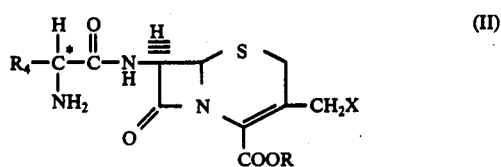

wherein X is hydrogen, lower alkanoyloxy, or heterothio can be reacted, preferably in the form of its trifluoroacetic acid salt, with a 2,4-dioxo-1-imidazolidine compound of the formula

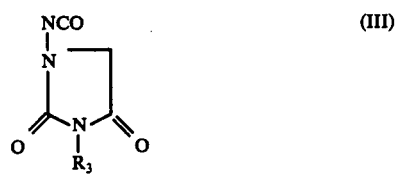

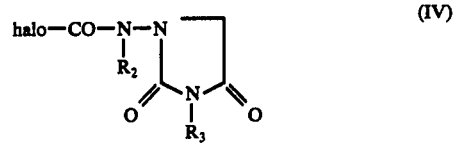

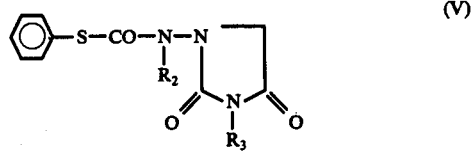

wherein $R_2$ and $R_3$ are as defined above and halo is chlorine or bromine, to yield the compound of formula I wherein $R_1$ is hydrogen and X is hydrogen, lower alkanoyloxy or heterothio.

The α-amino intermediate of formula II can be prepared by various methods such as by acylating a 7-amino cephalosporin of the formula

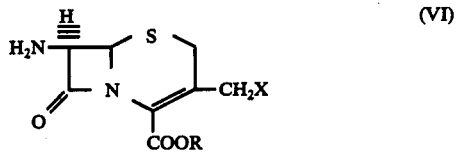

with a substituted α-amino acid of the formula

wherein Y is a protecting group such as

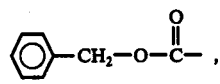

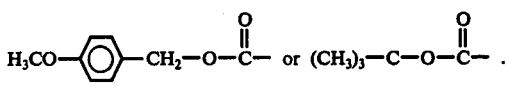

The α-amino protecting group is then removed by treating the resulting cephalosporin with trifluoroacetic acid and anisole. The α-amino compounds of formula II are taught in various U.S. Pat. Nos. as for example, 3,485,819; 3,507,861; 3,641,021; 3,796,801; 3,813,388; 3,821,207, etc.

Similarly, the 7α-methoxy compounds of formula I ($R_1$ is methoxy) wherein X is hydrogen, lower alkanoyloxy or heterothio can be prepared by reacting an α-amino intermediate of the formula

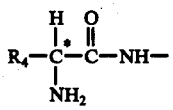
(VIII)

preferably in the form of its trifluoroacetic acid salt with a compound of formula III, IV or V.

The 7α-methoxy intermediates of formula VIII can be prepared in an analogous manner to the compound of formula II, i.e., by acylating a 7α-methyl-7β-aminocephalosporin of the formula

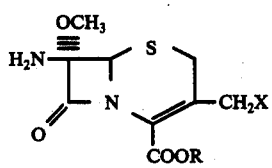
(IX)

with a substituted α-amino acid of formula VII followed by removal of the protecting group. The compounds of formula IX are taught in U.S. Pat. No. 3,897,424 and the preparation of the compound of formula VIII by various other methods are taught in U.S. Pat. Nos. 3,775,410; 3,780,031; 3,780,033; 3,780,034; 3,780,037; 3,887,549, etc.

The compounds of formula I wherein $R_1$ is either hydrogen or methoxy and X is pyridinium or carbamoyl substituted pyridinium are prepared by reacting the compound of the formula

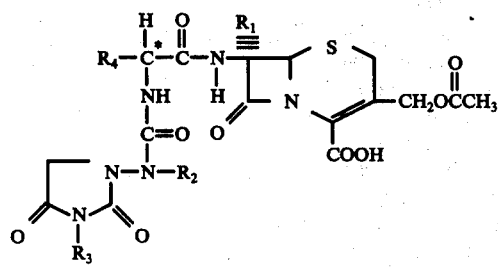
(Ib)

with pyridine or carbamoyl substituted pyridine (e.g., isonicotinamide) in a polar solvent such as water and in the presence of a catalyst such as an alkali metal thiocyanate. U.S. Pat. No. 3,792,047 and German Offenlegungsschrift 2,234,280 both disclose methods for reacting a cephalosporin so as to replace an acetoxy group with a pyridinium group.

Also, the compounds of formula I wherein $R_1$ is either hydrogen or methoxy and X is heterothio can be prepared by reacting the compound of formula Ib with a mercaptan of the formula (X) hetero-S-H or an alkali metal (preferably sodium) salt thereof of the formula (XI) hetero-S-alkali metal Methods for displacing the acetoxy group of a cephalosporin by a heterothio group are taught in various U.S. Pat. Nos. including 3,855,213; 3,890,309; 3,892,737, etc.

The compounds of formula I wherein $R_3$ is hydrogen or lower alkyl and X is hydrogen, acetoxy or heterothio can also be prepared by reacting a compound of the formula

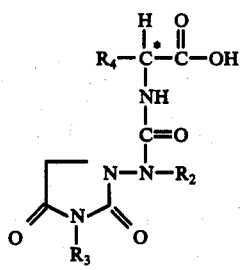
(XII)

or a derivative thereof wherein the hydroxy group is replaced with a known activating group, with an ester, e.g. trimethylsilyl or diphenylmethyl ester, of the compound of formula VI or IX, optionally in the presence of dicyclohexylcarbodiimide. The resulting ester is then treated according to methods known in the art, e.g., with water or with trifluoroacetic acid and anisole to yield the corresponding compound of formula I wherein R is hydrogen.

The compound of formula XII is prepared by reacting the isocyanate acid ester of the formula

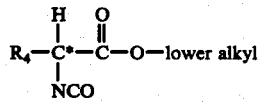
(XIII)

with the 1-amino-2,4-dioxoimidazolidine of the formula

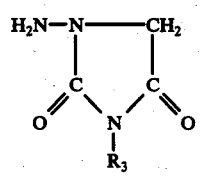
(XIV)

or by reacting an α-amino acid of the formula

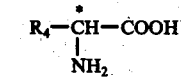
(XV)

preferably an ester like the trimethylsilyl ester, with the acyl halide of formula IV, in an organic medium like acetonitrile.

The starting materials of formula XIII are produced from the corresponding α-amino acid by reaction with phosgene in toluene by the method of Goldschmidt et al., Annalen der Chemie 575, 217 (1951). The 1-amino-2,4-dioxoimidazolidines of formula XIV are produced according to the method described in Monatsch 85, 607 (1954).

The compounds of formula I wherein R is lower alkyl, phenyl-lower alkyl, trihaloethyl, diphenyl-lower alkyl or the acyloxymethyl group

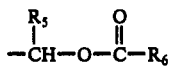

are obtained by reacting the 7-aminocephalosporin of formula VI or IX either before or after the acylation of the 7-aminosubstituent with one or two moles of a compound of the formula (XV) halo-R or (XVI) R=N⁺=N⁻ wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the cephalosporanic acid moiety either before or after the acylation reaction.

The carboxylate salts of the compound of formula I are formed by reacting the carboxyl group of the cephalosporanic acid moiety, i.e., R is hydrogen, with any of the salt forming ions described above.

Additional experimental details are found in the examples.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and alkali metal salts of formula I (i.e., R is hydrogen, alkali metal, especially sodium or potassium, or diphenylmethyl); wherein X is hydrogen, lower alkanoyloxy, especially acetoxy, pyridinium, carbamoyl substituted pyridinium (particularly where the carbamoyl group is in the 4-position), 1-methyltetrazolylthio or 5-methyl-1,3,4-thiadiazolylthio; R₁ is hydrogen or methoxy, especially hydrogen; R₄ is cyclohexadienyl, phenyl, benzyl, phenethyl, substituted phenyl, benzyl or phenethyl wherein the substituent is on the phenyl ring and is one or two members selected from chloro, bromo, methyl, ethyl, methoxy, ethoxy and hydroxy or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl or ethyl; R₂ and R₃ each is hydrogen.

Compounds of formula I wherein X is

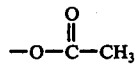

and R₂, R₃ and R₄ are as defined above are preferred as both final products and intermediates.

The most preferred final compounds are the acids and alkali metal salts of formula I wherein R₄ is 2-thienyl, 3-thienyl, phenyl or 4-hydroxyphenyl; and X is heterothio, particularly wherein X is

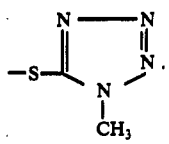

The compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter hafniae, Enterobacter cloacae, Klebsiella pneumoniae, Serratia marcescens*, etc. They may be used as antibacterial agents in a prophylactic manner or to combat infections due to organisms such as those named above, and in general may be utilized in a manner similar to cephalothin and other cephalosporins. For example, a compound of formula I or a physiologically acceptable salt thereof may be used in various mammalian species such as mice, rats, dogs, etc., in an amount of about 1 to 100 mg./kg., daily, orally or parenterally, in single or two to four divided doses to treat infections of bacterial origin, e.g., 5.0 mg./kg. in mice.

About 10 to 400 mg. of an acid compound of formula I or a physiologically acceptable salt thereof can be incorporated in an oral dosage form such as tablet, capsule or elixir or in an injectable form in a sterile aqueous vehicle. The substance is compounded with a physiologically acceptable vehicle, excipient, binder, preservative, stabilizer, flavor, etc., in a unit dosage form as called for by accepted pharmaceutical practice. The amount of active substance in these compositions or preparations is such that a suitable dosage in the range indicated is provided.

Illustrative of the adjuvants which may be incorporated in tablets, capsules and the like are the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; a sweetening agent such as sucrose, lactose or saccharin; a flavoring agent such as peppermint, oil of wintergreen or cherry. When the dosage unit form is a capsule, it may contain in addition to materials to the above type a liquid carrier such as a fatty oil. Various other materials may be present as coatings or to otherwise modify the physical form of the dosage unit. For instance, tablets or capsules may be coated with shellac, sugar or both. A syrup or elixir may contain the active compound, sucrose as a sweetening agent, methyl and propyl parabens as preservatives, a dye and a flavoring such as cherry or orange flavor. Of course, any material used in preparing the dosage unit should be pharmaceutically pure and substantially non-toxic in the amounts employed.

Injectable compositions are prepared by dissolving or suspending the active substance in a sterile vehicle such as water for injection or a natural vegetable oil such as sesame oil, cottonseed oil, peanut oil, soybean oil or the like or a synthetic fatty vehicle such as ethyl oleate. Antioxidants, buffers, preservatives and the like may also be included. The material can also be prepared in the dry form for reconstitution with such vehicles.

The following examples are illustrative of the invention and constitute especially preferred embodiments. They also serve as models for the preparation of other members of the group which can be produced by suitable substitution of starting materials. All temperatures are in degrees celsius.

EXAMPLE 1 a. D-2-[[[(4-Methoxyphenyl)methoxy]carbonyl]amino]-2-thiopheneacetic acid 74 g. of D-2-thienylglycine are dissolved in 940 ml. of water. 37.8 g. of magnesium oxide are added and to this resulting suspension a solution of 107.5 g. of p-methoxybenzyloxycarbonylazide in 940 ml. of dioxane is added with stirring. The mixture is stirred at room temperature for 24 hours. It is then filtered and the filtrate is extracted with 600 ml. of ether. The extract is discarded. The water in dioxane phase is layered over with 600 ml. of ethyl acetate, cooled to 5° and brought to pH 2 with 2N hydrochloric acid. The layers are separated and the aqueous layer is again extracted with 300 ml. of ethyl acetate. The combined ethyl acetate extracts are washed with water, dried with magnesium sulfate, filtered and concentrated. The oily residue crystallizes upon trituration with petroleum ether to yield 118 g. of D-2-[[[(4-methoxyphenyl)methoxy]carbonyl]amino]-2-thiopheneacetic acid; m.p. 84°–94°; $[\alpha]_{20}^{D}$: $-69°$ (c=1, tetrahydrofuran).

b. 7β-Amino-3-[[(1-methyl-1H-tetrazolyl-5-yl)thio]methyl]-8-oxo-5-thia-1-azabicyclo[4.2.0]oct-2-ene-2-carboxylic acid To a stirred suspension of 27.2 g. of 7-amino cephalosporanic acid (0.1 mole) in 150 ml. of acetone and 100 ml. of water at 0°–5° is added 50 ml. of 2N sodium hydroxide, with care being taken to keep the pH below 8.5. A solution of 12.7 g. (0.11 mole) of 1-methyl-5-mercapto-1H-tetrazole in 50 ml. of 2N sodium hudroxide is added, and the mixture is allowed to warm to room temperature. The stirred mixture is then maintained at 60° (internal temperature) under nitrogen for 3 hours at pH 7–7.5 by the periodic addition of dilute aqueous sodium hydroxide. The mixture is cooled in an ice-water bath, and while stirring, 3N HCl is added to adjust the pH to 3.9. Stirring is continued for 15 minutes, and the precipitate is collected by filtration, washed with water, and then acetone, and finally dried to give the desired product as a powder (18.4 g.).

c. 7β-Amino-3-[[(1-methyl-1H-tetrazol-5-yl)thio]methyl]-8-oxo-5-thia-1-azabicyclo[4.2.0]oct-2-ene-2-carboxylic acid, diphenylmethyl ester A mixture of 16.4 g. (0.05 mole) of the acid product from part (b), 10.3 g. (0.054 mole) of p-toluenesulfonic acid monohydrate, 350 ml. of dioxane (dried by passage through basic alumina), and dry CH₃OH is stirred at room temperature under nitrogen for 30 minutes. The clear solution is evaporated to a residue, and water and CH₃OH are removed by four evaporations of 100 ml. quantities of dioxane. Fresh dioxane (300 ml.) is then added to the residue followed by a solution of crystalline diphenyldiazomethane (19.4 g., 0.01 mole) in 150 ml. of dry dimethoxyethane. The mixture is initially shaken vigorously for 10–15 minutes and then stirred at room temperature for 3 hours. Methanol (25 ml.) is added, and the red solution is stirred until it has turned yellow-orange. The solvents are removed in vacuo, and the residue is treated with 400 ml. of CH₂Cl₂ and a solution of 20 g. of K₂HPO₄ in 250 ml. of water. The CH₂Cl₂ layer is washed with water and saturated NaCl, and finally dried (MgSO₄) to give a residue after removal of the solvent in vacuo. Treatment of the residue with Et₂O gives a solid (27 g.). Column chromatography of this solid on silica gel by elution with CHCl₃ and then EtOAc-CHCl₃ (4:1) provides the desired product as a residue (12.9 g.). Treatment with EtOAc then provides 8.0 g. of the desired product as a pale yellow powder.

d. 7β-[[D-[[[(4-Methoxyphenyl)methoxy]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 46.2 g. of 7β-amino-3-[[(1-methyl-1-H-tetrazol-5-yl)-thio]methyl]-8-oxo-5-thia-1-azabicyclo[4.2.0]oct-2-ene-2-carboxylic acid, diphenylmethyl ester from part (c) are dissolved in 550 ml. of anhydrous methylene chloride. 550 ml. of tetrahydrofuran and 36 g. of D-2-[[[(4-methoxyphenyl)-methoxy]carbonyl]amino]-2-thiopheneacetic acid, from part (a), are added. The reaction solution is cooled to 0° and a solution of 22.5 g. of dicyclohexylcarbodiimide in 150 ml. of anhydrous tetrahydrofuran is added dropwise over the course of 30 minutes. The mixture is then stirred for 90 minutes at 0° and finally 120 minutes at room temperature. The precipitated dicyclohexylurea (21 g.) is filtered off under suction and the filtrate is concentrated. The residue is taken up in a mixture of 1000 ml. of ethyl acetate and 400 ml. of tetrahydrofuran, filtered and the filtrate is washed first with sodium bicarbonate solution and then with water. This is then dried with magnesium sulfate, treated with activated carbon, filtered and the filtrate is then concentrated slowly under vacuum to a small volume. After standing overnight in the refrigerator, the precipitated crystals are filtered under suction to obtain 63.1 g. of 7β[[D-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester, m.p. 130°–131° (dec.). $[\alpha]_{20}^{D}$ $-117°$ (c = 1, tetrahydrofuran).

e. 7β-[D-2-Amino-2-(2-thienyl)acetamido]-3-[[(1-methyl-1H-tetrazol-5-yl)thio]methyl]-8-oxo-5-thia-1-azabicyclo-[4.2.0]oct-2-ene-2-carboxylic acid, trifluoroacetic acid salt (1:1)

62 g. of the diphenylmethyl ester product from part (d) are added to 300 ml. of anisole with stirring. The mixture is cooled to 0° and 750 ml. of trifluoroacetic acid are added slowly. The mixture is stirred for 10 minutes at 0° and the anisole is evaporated at 0.1 mm. of Hg and 35° bath temperature. The residue is treated with 250 ml. of petroleum ether, then 350 ml. of ether, stirred for one hour, and filtered with suction to yield 46.4 g. of 7β-[D-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1); m.p. 138°–139° (dec.).

EXAMPLE 2 a.
L-2-[[[(4-Methoxyphenyl)methoxy]carbonyl]amino]-2-thiopheneacetic acid

L-2-Thienylglycine and p-methoxybenzyloxycarbonylazide are reacted according to the procedure of Example 1 (a) to yield L-2-[[[(4-methoxyphenyl)methoxy]carbonyl]amino]-2-thiopheneacetic acid; m.p. 97°-98°; $[\alpha]_D^{25}$ +68° (c = 1, tetrahydrofuran).

b.
7β-[[L-[[[(4-Methoxyphenyl)methoxy]carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 4.6 g. of L-2-[[[(4-methoxyphenyl)methoxy]carbonyl]-amino]-2-thiopheneacetic acid from part (a) and 5.9 g. of 7β-amino-3-[[(1-methyl-1H-tetrazol-5-yl)thio]-methyl]-8-oxo-5-thia-1-azabicyclo[4.2.0]oct-2-ene-2-carboxylic acid, diphenylmethyl ester from Example 1(c) are reacted according to the procedure of Example 1(d) to yield 8.4 g. of 7β-[[L-[[[(4-methoxyphenyl)methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester which after concentration and treating with ether is obtained is amorphous form.

c.
7β-[L-2-Amino-2-(2-thienyl)acetamido]-3-[[(-1-methyl-1H-tetrazol-5-yl)thio]methyl]-8-oxo-5-thia-1-azabicyclo[4.2.0]-oct-2-ene-2-carboxylic acid, trifluoroacetic acid salt (1:1)

1.6 g. of the diphenylmethyl ester product from part (b) are treated with trifluoroacetic acid and anisole according to the procedure of Example 1 (e) to yield 1.1 g. of 7β-[L-2-amino-2-(2-thienyl)acetamido]-3-[[(1-methyl-1H-tetrazol-5-yl)thio]methyl]-8-oxo-5-thia-1-azabicyclo[4.2.0]-oct-2-ene carboxylic acid, trifluoroacetic acid salt (1:1); m.p. 127°-131° (dec.).

EXAMPLE 3 a.
D-2-[[[(4-Methoxyphenyl)methoxy]carbonyl]amino]-phenyl acetic acid

D-2-phenylglycine and p-methoxybenzyloxycarbonylazide are reacted according to the procedure of Example 1 (a) to yield D-2-[[[(4-methoxyphenyl)methoxy]carbonyl]amino]phenylacetic acid.

b.
7β-[[D-[[[(4-Methoxyphenyl)methoxy]carbonyl]-amino]-phenylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 12 g. (.025 mole) of 7β-amino-3-[[(1-methyl-1H-tetrazol-5-yl)thio]methyl]-8-oxo-5-thia-1-azabicyclo[4.2.0]-oct-2-ene-2-carboxylic acid, diphenylmethyl ester from Example 1 (c) and 7.7 g. (0.025 mole) of D-2-[[[(4-methoxyphenyl)methoxy]carbonyl]amino]-phenylacetic acid from part (a) are reacted in the presence of 6.2 g. (0.025 mole) of dicyclohexylcarbodiimide according to the procedure of Example 1 (d) to yield 16 g. of light beige 7β-[[D-[[[4-methoxyphenyl)methoxy]-carbonyl]amino]phenylacetyl]amino]-3-[[(1-methyl-1H-tetrazol-5-yl)thiomethyl]-8-oxo-5-thia-1-azabicyclo[4.2.0]oct-2-ene-2-carboxylic acid, diphenylmethyl ester, m.p. 147° (dec.)

c.
7β-[D-2-Amino-2-phenylacetamido[-3-[[(1-methyl-1H-tetrazol-5-yl)thio]methyl]-8-oxo-5-thia-1-azabicyclo-[4.2.0]oct-2-ene-2-carboxylic acid, trifluoroacetic acid salt (1:1)

16 g. of the diphenylmethyl ester product from part (b) are treated with trifluoroacetic acid and anisole according to the procedure of Example 1 (e) to yield 10.1 g. of 7β-[D-2-amino-2-phenylacetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt (1:1); m.p. 128°-130° (dec.).

EXAMPLE 4 a.
7α-Methoxy-7β-[[DL-[[[(4-methoxyphenyl)methoxy]-carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester 2.41 g. (.0075 mole) of DL-2-[[[(4-methoxyphenyl)-methoxy]carbonyl]amino]-2-thiopheneacetic acid (prepared according to the procedure of Example 1 (a) is dissolved in 50 ml. of dry methylene chloride, the solution is cooled in an ice bath to 0°-5°, and 0.969 g. (0.0075 mole) of diisopropylethylamine and isobutylchloroformate are added to the cold solution. After 10 minutes, 3.28 g. (.00625 mole) of 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester is added to the reaction mixture and the ice bath is removed. Following three hours of stirring at room temperature, a second portion of mixed anhydride is prepared in a separate flask using the procedure described above. This solution is added to the reaction mixture and after 4.5 hours another batch of mixed anhydride prepared using half the quantities set forth above is added to the main reaction mixture. Stirring is continued at room temperature for 12 hours and the reaction mixture is then diluted with methylene chloride and washed with water, saturated aqueous sodium bicarbonate solution, and water. The organic layer is dried over sodium sulfate and the solvent is removed in vacuo to yield a foam. This crude product is chromatographed on silica gel (200 g., 60-200 mesh) and the desired product is eluted with 9:1 and 4:1 methylene chloride: ethyl acetate. The oily product is precipitated as a powder from a methylene chloride-ether mixture and dried over phosphorus pentoxide in vacuo to yield 3.81 g. of 7α-methoxy-7β-[[DL-[[[(4-methoxyphenyl)-methoxy]carbonyl]amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester.

Alternatively, the same compound can be obtained by the following procedure:

129 mg. (0.4 mole) of DL-2-[[[(4-methoxyphenyl)methoxy]carbonyl]amino]-2-thiopheneacetic acid is dissolved in 2 ml. of anhydrous methylene chloride and 47 mg. (0.2 mmole) of dicyclohexylcarbodiimide is added. The mixture is stirred for 15 minutes at room temperature during which time colorless dicyclohexylurea crystallizes. The suspension is directly filtered into a stirring solution of 77 mg. (0.147 mmole) of 7β-amino-7α-methoxy-3-[[(1-methyl-1H-tetrazol-5-yl)thio]methyl]-8-oxo-5-thia-1-azabicyclo[4.2.0]oct-2-ene-2-carboxylic acid, diphenylmethyl ester in 1 ml. of methylene chloride. After stirring at room temperature for 19 hours, the mixture is diluted with methylene chloride, washed with pH 7.4 buffer, and dried over sodium sulfate. Removal of solvent under reduced pressure yields a crude oil which is chromatographed on preparative thin layer chromatography silica gel plates developed in a 4:1 chloroform:ethyl acetate mixture. The desired product (58 mg.) is isolated as an oil.

b.
7α-Methoxy-7β-[DL-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt The diphenylmethyl ester product from part (a) is reacted with trifluoroacetic acid in the presence of anisole according to the procedure of Example 1 (e) to yield 7α-methoxy-7β-[DL-2-amino-2-(2-thienyl)acetamido]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt.

EXAMPLE 5

α-[[[(2,4-dioxo-1-imidazolidinyl)amino]carbonyl]-amino]-benzeneacetic acid, ethyl ester 1.15 g. (0.01 mol.) of 1-amino-2,4-dioxoimidazolidine are dissolved in 50 ml. of dioxane while heating. The solution is permitted to cool to room temperature while stirring, wherein a portion of the 1-amino-2,4-dioxoimidazolidine crystallizes out. 2.05 g. (0.01 mol.) of α-cyanatobenzeneacetic acid, ethyl ester are added and the reaction mixture is stirred overnight at room temperature. On the next day the mixture is concentrated and the residue is triturated with ether. 3.0 g. of α-[[[(2,4-dioxo-1-imidazolidinyl)amino]-carbonyl]amino]-benzeneacetic acid, ethyl ester are obtained, m.p. 148°-151°.

EXAMPLE 6

α-[[[(2,4-dioxo-1-imidazolidinyl)amino]carbonyl]-amino]benzene acetic acid 29.4 g. of α-[[[(2,4-dioxo-1-imidazolidinyl)amino]-carbonyl]amino]benzeneacetic acid, ethyl ester are added to 138 ml. of 2N sodium hydroxide solution with stirring. The substance goes quickly into solution upon slight heating. The mixture is stirred for 2 hours at room temperature, filtered and the clean filtrate is acidified to pH 1 with concentrated hydrochloric acid. Upon rubbing, α-[[[(2,4-dioxo-1-imidazolidinyl)amino]carbonyl]-amino]benzene acetic acid crystallizes out. The mixture is let stand in the refrigerator overnight and then filtered under suction, yield 21.9 g., m.p. 139°-143°.

EXAMPLE 7

3-[(Acetoxy)methyl]-7β-[[[[(2,4-dioxo-1-imidazolidinyl)amino]carbonyl]amino]phenylacetyl]-amino]-8-oxo-5-thia-1-azabicyclo[4.2.0]oct-2-ene-2-carboxylic acid, diphenylmethyl ester 3.62 g. (0.012 mol.) of α-[[[(2,4-dioxo-1-imidazolidinyl)amino]carbonyl]amino]benzeneacetic acid are dissolved in 150 ml. of tetrahydrofuran, 4.38 g. (0.01 mol.) of 3-acetyloxymethyl-7-amino-8-oxo-5-thia-1-azabicyclo[4.2.0]oct-2-ene-2-carboxylic acid, diphenylmethyl ester are added and 2.27 g. of dicyclohexylcarbodiimide dissolved in 40 ml. of tetrahydrofuran are added dropwise with stirring at 0°-5° to the clear solution over a period of 10 minutes. The reaction mixture is stirred for 90 minutes at 0°-5° and 90 minutes at room temperature. The mixture is filtered and the filtrate is concentrated. The residue is triturated with ether and filtered under suction. 7.8 g. of crude 3-[(acetyloxy)-methyl]-7β-[[[[(2,4-dioxo-1-imidazolidinyl)amino]carbonyl]-amino]phenylacetyl]amino]-8-oxo-5-thia-1-azabicyclo[4.2.0]-oct-2-ene-2-carboxylic acid, diphenylmethyl ester are obtained. The crude product is purified by adding it to 100 ml. of methylene chloride and stirring for 2 hours. After filtering under suction, 5.7 g. of product are obtained, m.p. 190°-196° (dec.). By adding petroleum ether to the filtrate, an additional 1.5 g. of not as pure product are obtained.

EXAMPLE 8

3-[(Acetyloxy)methyl]-7β-[[[[(2,4-dioxo-1-imidazolidinyl)-amino]carbonyl]amino]phenylacetyl]-amino]-8-oxo-5-thia-1-azabicyclo[4.2.0]oct-2-ene-2-carboxylic acid 1.5 g. of 3-[(acetyloxy)methyl]-7β-[[[[(2,4-dioxo-1-imidazolidinyl)amino]carbonyl]amino]phenylacetyl]-amino]-8-oxo-5-thia-1-azabicyclo[4.2.0]oct-2-ene-2-carboxylic acid, diphenylmethyl ester are added to a mixture of 30 ml. of trifluoroacetic acid and 9 ml. of anisole, the mixture is stirred for 10 minutes, concentrated in vacuum and ether is added. 1.1 g. of 3-[(acetyloxy)methyl]-7β-[[[[(2,4-dioxo-1-imidazolidinyl)amino]carbonyl]amino]phenylacetyl]amino]-8-oxo-5-thia-1-azabicyclo[4.2.0]oct-2-ene-2-carboxylic acid are obtained, m.p. 205°-212°. This product is converted to its sodium salt by dissolving 1 gm. in 30 ml. of acetone, adding 18 ml. of 0.1 N sodium bicarbonate solution, distilling off the acetone in vacuum, filtering and freeze drying the filtrate, yield 1.0 g., m.p. 228°-230° (dec.).

EXAMPLE 9

7β-[[[[(2,4-dioxo-1-imidazolidinyl)amino]carbonyl]-amino]-phenylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 2.47 g. (0.005 mol.) of 7-amino-3-[[(1-methyl-1H-tetrazol-5-yl)thio]methyl]-8-oxo-5-thia-1-azabicyclo[4.2.0]-oct-2-ene-2-carboxylic acid, diphenylmethyl ester are dissolved in a mixture of 30 ml. of methylene chloride and 100 ml. of tetrahydrofuran and 1.81 g. (0.006 mol.) of α-[[[(2,4-dioxo-1-imidazolidinyl)amino]-carbonyl]amino]benzenacetic acid are added. To the clear solution is added dropwise at 0°-5° with stirring a solution of 1.13 g. (0.0055 mol.) of dicyclohexylcarbodiimide in 20 ml. of tetrahydrofuran. The mixture is then stirred for 90 minutes at 0°-5° and 90 minutes at room temperature. This is then filtered, the filtrate is evaporated to dryness, the residue is dissolved in 300 ml. of ethyl acetate, filtered and concentrated to a volume of 30 ml. 2.6 g. of 7β-[[[[(2,4-dioxo-1-imidazolidinyl-)amino]carbonyl-amino]phenylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester crystallize. By concentrating the filtrate, an additional 1.4 g. of the product are obtained, m.p. 183°-187° (dec.).

EXAMPLE 10

7β-[[[[[(2,4-dioxo-1-imidazolidinyl)amino]carbonyl]-amino]phenyl-acetyl]amino-3-[[(1-methyl-1H-tetrazol-5-yl)thio]methyl]-8-oxo-5-thia-1-azabicyclo[4.2.0]oct-2-ene-2-carboxylic acid The 7β-[[[[[(2,4-dioxo-1-imidazolidinyl)amino]-carbonyl]aminophenylacetyl]amino]-3-[[(1-methyl-1H-tetrazol-5-yl)thio]methyl]-8-oxo-5-thia-1-azabicyclo[4.2.0]oct-2-ene-2-carboxylic acid, diphenylmethyl ester obtained in Example 9 is reacted with trifluoroacetic acid and anisole according to the procedure of Example 8 to obtain 7β-[[[[[(2,4-dioxo-1-imidazolidinyl)amino]carbonyl]amino]phenylacetyl]amino]-3-[[(1-methyl-1H-tetrazol-5-yl)thio]methyl]-8-oxo-5-thia-1-azabicyclo[4.2.0]oct-2-ene-2-carboxylic acid, m.p. 170°-178° (dec.). This acid is converted to its sodium salt by treatment with an equimolar amount of 0.1 N sodium bicarbonate solution, filtering and freeze drying the filtrate, m.p. 207°-212°.

EXAMPLE 11

3-[[4-(Aminocarbonyl)pyridinio]methyl]-8-oxo-7β-[[[[[(2,4-dioxo-1-imidazolidinyl)amino]carbonyl]-amino]phenylacetyl]-amino]-5-thia-1-azabicyclo[4.2.0]-oct-2-ene-2-carboxylic acid inner salt.

A mixture of 0.455 g. of 3-[(acetyloxy)methyl]-7β-[[[[[(2,4-dioxo-1-imidazolidinyl)amino]carbonyl]-amino]-phenylacetyl]amino]-8-oxo-5-thia-1-azabicyclo[4.2.0]oct-2-ene-2-carboxylic acid, sodium salt, 0.146 g. of 4-pyridinecarboxamide, 1.92 g. of potassium thiocyanate and 1.2 ml. of water are heated at 50° for 24 hours. A chromatography column is filled with 30 g. of ion exchange resin (Amberlite XAD-2). 20 g. of a paste of the same ion exchange resin is admixed with the reaction mixture, stirred for 30 minutes and the mixture is poured into the column. The column is eluted with 750 ml. of water, then with a mixture of water and methanol (8.2). The eluate is collected in 10 ml. portions. Fractions 95-120 are concentrated and freeze dried to obtain 85 mg. of 3-[[4-aminocarbonyl)pyridinio]-methyl]-8-oxo-7β-[[[[[(2,4-dioxo-1-imidazolidinyl)amino]-carbonyl]amino]phenylacetyl]amino]-5-thia-1-azabicyclo[4.2.0]oct-2-ene-2-carboxylic acid, inner salt, m.p. 183°-186° (dec.).

EXAMPLE 12

DL-α-[[[(2,4-dioxo-1-imidazolidinyl)amino]carbonyl]-amino]-2-thiopheneacetic acid, ethyl ester By reacting 10.60 g. of DL-α-isocyanato-2-thiopheneacetic acid, ethyl ester with 5.75 g. of 1-amino-2,4-dioxoimidazolidine in 250 ml. of dioxane according to the procedure of Example 5, 15.6 g. of DL-α-[[[(2,4-dioxo-1-imidazolidinyl)-amino]carbonyl]amino]-2-thiopheneacetic acid, ethyl ester is obtained, m.p. 151°-155°.

EXAMPLE 13

DL-α-[[[(2,4-dioxo-1-imidazolidinyl)amino]carbonyl]-amino]-2-thiopheneacetic acid By mixing the DL-α-[[[(2,4-dioxo-1-imidazolidinyl)-amino]carbonyl]amino]-2-thiopheneacetic acid, ethyl ester, obtained in Example 12, with sodium hydroxide solution and then acidifying according to the procedure of Example 6, DL-α-[[[(2,4-dioxo-1-imidazolidinyl)amino]carbonyl]amino]-2-thiopheneacetic acid is obtained, m.p. 193° (dec.).

EXAMPLE 14

7β-[[DL-[[[(2,4-dioxo-1-imidazolidinyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid, diphenylmethyl ester 2.1 g. of DL-α-[[[(2,4-dioxo-1-imidazolidinyl)amino]-carbonyl]amino]-2-thiopheneacetic acid and 2.47 g. of 7-amino-3-[[[(1-methyl-1H-tetrazol-5-yl)thio]methyl]-8-oxo-5-thia-1-azabicyclo[4.2.0]oct-2-ene-2-carboxylic acid, diphenylmethyl ester are made to react with dicyclocarbodiimide according to the procedure of Example 9 to obtain 4.3 g. of 7β-[[DL-[[[2,4-dioxo-1-imidazolidinyl)amino]carbonyl]amino]-2-thienylacetyl]amino]-3-[[(1-methyl-1H-tetrazol-5-yl)thio]-methyl]-8-oxo-5-thia-1-azabicyclo[4.2.0]-oct-2-ene-2-carboxylic acid, diphenylmethyl ester, 136°-175° (dec.).

EXAMPLE 15

7β-[[DL-[[[2,4-dioxo-1-imidazolidinyl)amino]carbonl]amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid The 7β-[[DL-[[[2,4-dioxo-1-imidazolidinyl)amino]-carbonyl]amino]-2-thienylacetyl]amino]-3-[[(1-methyl-1H-tetrazol-5-yl)-thio]methyl]-8-oxo-5-thia-1-azabicyclo[4.2.0]oct-2-ene-2-carboxylic acid, diphenylmethyl ester obtained in Example 14 is treated with trifluoroacetic acid and anisole according to the procedure of Example 8, to obtain 7β-[[DL-[[[2,4-dioxo-1-imidazolidinyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, m.p. 160°-180° (dec.). The sodium salt is obtained by treating this product with an equimolar amount of sodium bicarbonate in water, filtering and freeze drying the filtrate, m.p. 200°-220° (dec.).

EXAMPLE 16

D-α-[[[(2,4-dioxo-1-imidazolidinyl)amino]carbonyl]-amino]-2-thiopheneacetic acid, 4-nitrophenyl ester 1.15 g. (0.01 mol.) of 1-amino-2,4-dioxoimidazolidine are dissolved in 50 ml. of anhydrous dioxane by warming. On cooling to room temperature, the 1-amino-2,4-dioxoimidazolidine crystallizes out in finely divided crystalline form. 0.01 mol. of D-α-isocyanato-2-thiopheneacetic acid, 4-nitrophenyl ester is added and the mixture is stirred at room temperature overnight. A turbidity forms which is filtered off and the filtrate is concentrated. The wax-like residue is triturated with ether and filtered under suction to obtain 3.8 g. of D-α-[[[(2,3-dioxo-1-imidazolidinyl)amino]carbonyl)]-amino]-2-thiopheneacetic acid, 4-nitrophenyl ester, m.p. 170°-174°.

EXAMPLE 17

7β-[[D-[[[(2,4-dioxo-1-imidazolidinyl)amino]carbonyl]-amino]-2-thienylacetyl]amino]-3-[[(1-methyl-1H-tetrazol-5-yl)thio]methyl[-8-oxo-5-thia-1-azabicyclo[4.2.0]-oct-2-ene-2-carboxylic acid, diphenylmethyl ester A solution of 3.46 g. (0.007 mol.) of 7-amino-3-[[(1-methyl-1H-tetrazol-5-yl)thio]methyl]-8-oxo-5-thia-1-azabicyclo[4.2.0]oct-2-ene-2carboxylic acid, diphenylmethyl ester in 46 ml. of methylene chloride is admixed with a solution of 3.52 g. of D-α-[[[(2,4-dioxo-1-imidazolidinyl)-amino]carbonyl]amino-2-thiopheneacetic acid, 4-nitrophenyl ester in 23 ml. of dimethylacetamide. 1.42 g. (0.084 mol.) of N-hydroxybenzothiazole are added to the mixture which is then heated at 40° for 24 hours. 6.2 g. of 7β-[[D-[[[(2,4-dioxo-1-imidazolidinyl)amino]carbonyl]amino]-2-thienylacetyl]-amino]-3-[[(1-methyl-1H-tetrazol-5-yl)thio]methyl]-8-oxo-5-thia-1-azabicyclo[4.2.0]-oct-2-ene-2-carboxylic acid, diphenylmethyl ester are obtained which are purified by precipitating from ethyl acetate-ether, m.p. 130°-140° (dec.).

EXAMPLE 18

7β-[[D-[[[(2,4-dioxo-1-imidazolidinyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]oct-2-ene-2-carboxylic acid 7β-[[D-[[[(2,4-dioxo-1-imidazolidinyl)amino]carbonyl]-amino]-2-thienylacetyl]amino]-3-[[(1-methyl-1H-tetrazol-5-yl)thio]methyl]-8-oxo-5-thia-1-azabicyclo[4.2.0]oct-2-ene-2-carboxylic acid is obtained by treating the diphenyl ester obtained in Example 17 with trifluoroacetic acid and anisole according to the procedure of Example 8. The product is converted to its sodium salt by treatment with an equivalent proportion of sodium bicarbonate solution according to the procedure described in the same Example.

EXAMPLE 19

1-[[(Phenylthio)carbonyl]amino]-2,4-dioxoimidazolidine 1.15 g. of 1-amino-2,4-dioxoimidazolidine are dissolved in 35 ml. of hot dioxane. Upon cooling, the compound crystallizes out in finely divided form. The suspension thus obtained is added dropwise to a solution of 0.8 ml. of (phenylthio)carbonyl chloride in 10 ml. of dioxane. The mixture is stirred for 2 hours at room temperature. A precipitate of 1-amino-2,4-dioxoimidazolidine hydrochloride is filtered off under suction and the filtrate is evaporated on a rotary evaporator. The solid residue is triturated with a little ether and after standing for a while is filtered under suction to obtain 1.0 g. of 1-[[(phenylthio)carbonyl]amino]-2,4-dioxoimidazolidine, m.p. 152°-155°.

EXAMPLE 20

7β-[[L-[[(2,4-dioxo-1-imidazolidinyl)amino]carbonyl]-amino]-2-thienylacetyl]amino-3-[[(1-methyl-1H-tetrazol-5-yl)thio]methyl-8-oxo-5-thia-1-azabicyclo[4.2.0]-oct-2-ene-2-carboxylic acid 1.75 g. (0.003 mol.) of 7β-[L-[2-amino-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, trifluoroacetic acid salt are suspended in 15 ml. of anhydrous dioxane, 1.5 ml. (0.0105 mol.) of triethylamine are added, then to the solution obtained is added a solution of 0.9 g. (0.0036 mol.) of 1-[[(phenylthio)carbonyl]amino[-2,4-dioxoimidazolidine. After stirring for 4 hours, the mixture is diluted with a copious amount of ether and the precipitate is filtered under suction to obtain 7β-[[L-[[[(2,4-dioxo-1-imidazolidinyl)amino]carbonyl]amino]-2-thienylacetyl]amino]-3-[[(1-methyl-1H-tetrazol-5-yl)thio]methyl]-8 -oxo-5-thia-1-azabicyclo-[4.2.0]-oct-2-ene-2-carboxylic acid, triethylamine salt. This product is dissolved in water and acidified with 2N hydrochloric acid. 7β-[[L-[[(2,4-dioxo-1-imidazolidinyl)amino]-carbonyl]amino]-2-thienylacetyl]amino-3-[[(1-methyl-1H-tetrazol-5-yl)thio]methyl-8-oxo-5-thia-1-azabicyclo[4.2.0]oct-2-ene-2-carboxylic acid precipitates. The sodium salt is formed by dissolving the free acid with an equivalent amount of sodium bicarbonate solution and the salt is isolated by freeze drying.

EXAMPLE 21

1-(Chlorocarbonylamino)-2,4-dioxoimidazolidine 11.5 g. (0.1 mol.) of 1-amino-2,4-dioxoimidazolidine are thoroughly stirred into 150 ml. of absolute tetrahydrofuran. A solution of 15 g. (0.15 mol.) of phosgene in 25 ml. of absolute tetrahydrofuran is added dropwise at 0°-5° over 20 minutes. The mixture is then stirred for 3 hours at room temperature. An almost clear solution results. This is filtered and the solvent is evaporated in vacuum. The oily residue crystallizes on trituration with petroleum ether to obtain 1-(chlorocarbonylamino)-2,4-dioxoimidazolidine, yield 17.2 g., m.p. 126° (dec.).

EXAMPLE 22

7β-[[D-[[[(2,4-dioxo-1-imidazolidinyl)amino]carbonyl]-amino]-2-thienylacetyl]amino]-3-[[(1-methyl-1H-tetrazol-5-yl)thio]-methyl]-8-oxo-5-thia-1-azabicyclo[4.2.0]-oct-2-ene-2-carboxylic acid 10 g. (0.0171 mol.) of 7β-[D-[2-amino-2-thienylacetyl]-amino]-3-[[(1-methyl-1H-tetrazol-5-yl)thio]methyl]-8-oxo-5-thia-1-azabicyclo[4.2.0]oct-2-ene-2-carboxylic acid, trifluoroacetic acid salt, are added to 140 ml. of anhydrous acetonitrile. The substance partially goes into solution. Under nitrogen protection, 34.5 ml. of 1,2-propylene oxide and then 17.2 ml. of bis(trimethylsilyl)acetamide are added. A clear solution is obtained. A solution of 3.7 g. (0.021 mol.) of 1-(chlorocarbonylamino)-2,4-dioxoimidazolidine in 50 ml. of anhydrous acetonitrile is added dropwise with stirring at 0° over 15 minutes, then the mixture is stirred 30 minutes at 0° and 90 minutes at room temperature.

The reaction mixture is cooled to 10°, 50 ml. of water are added and the mixture is stirred vigorously for 5 minutes. Then 300 ml. of ethyl acetate are added and it is stirred for a short time. The phases are separated and the aqueous phase is extracted with 2 × 50 ml. of ethyl acetate. The combined extracts are washed with 2 × 50 ml. of water, dried with magnesium sulfate, treated with activated charcoal and concentrated in vacuum until crystallization begins. Then 50 ml. of ethyl acetate are again added to promote crystallization. The product, 7β-[[D-[[[(2,4-dioxo-1-imidazolidinyl)amino]carbonyl]-amino]-2-thienylacetyl]amino]-3-[[(1-methyl-1H-tetrazol-5-yl)thio]methyl]-8-oxo-5-thia-1-azabicyclo[4.2.0]-oct-2-ene-2-carboxylic acid, is washed with ethyl acetate and ether, yield 6.5 g., m.p. 198°-200°

(dec.). According to the NMR spectrum, the substance contains some ethyl acetate.

By dissolving the product in an equivalent proportion of sodium bicarbonate solution and freeze drying, the sodium salt is obtained, m.p. 199°–206°.

EXAMPLE 23

7β-[[DL-[[[(2,4-dioxo-1-imidazolidinyl)amino]carbonyl]amino]-2-thienylacetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid By substituting the 7α-methoxy-7β-[DL-2-amino-2-(2-thienyl)acetamido]-3-[[(1-methyl-1H-tetrazol-5-yl)thio]-methyl]-8-oxo-5-thia-1-azabicyclo[4.2.0]-oct-2-ene-2-carboxylic acid, trifluoroacetic acid salt of Example 4b in the procedure of Example 20, 7β-[[DL-[[[(2,4-dioxo-1-imidazolidinyl)amino]-carbonyl]-amino]-2-thienylacetyl]amino]-7α-methoxy-3-[[(1-methyl-1H-tetrazol-5-yl)thio]methyl]-8-oxo-5-thia-1-azabicyclo[4.2.0]oct-2-ene-2-carboxylic acid and its sodium salt are obtained.

EXAMPLE 24 a)

3-[(Acetyloxy)methyl]-7α-methoxy-7β-[[DL-[[[(4-methoxyphenyl)methoxy]carbonyl]amino]-2-thienylacetyl]amino]-8-oxo-5-thia-1-azabicyclo[4.2.0]-oct-2-ene-2-carboxylic acid, diphenylmethyl ester DL-2-[[[(4-methoxyphenyl)methoxy]carbonyl]-amino]-2-thiopheneacetic acid and 3-[(acetyloxy)methyl]-7α-methoxy-7β-amino-8-oxo-5-thia-1-azabicyclo[4.2.0oct-2-ene-2-carboxylic acid, diphenylmethyl ester are reacted according to the first procedure in Example 4 (a) to yield 3-[(acetyloxy)methyl]-7α-methoxy-7β-[[DL-[[[(4-methoxyphenyl)methoxy]carbonyl]amino]-2-thienylacetyl]amino]-8-oxo-5-thia-1-azabicyclo[4.2.0]oct-2-ene-2-carboxylic acid, diphenylmethyl ester.

b)

3-[(Acetyloxy)methyl]-7α-methoxy-7β-[DL-2-amino-2-(2-thienyl)acetamido]-8-oxo-5-thia-1-azabicyclo[4.2.0]-oct-2-ene-2-carboxylic acid, trifluoroacetic acid salt (1:1)

The diphenylmethyl ester product from part (a) is reacted with trifluoroacetic acid in the presence of anisole according to the procedure of Example 1 (e) to yield 3-[(acetyloxy)methyl]-7α-methoxy-7β-[DL-2-amino-2-(2-thienyl)acetamido]-8-oxo-5-thia-1-azabicyclo[4.2.0]-oct-2-ene-2-carboxylic acid, trifluoroacetic acid salt (1:1).

c)

3-[(Acetyloxy)methyl]-7α-methoxy-7β-[[DL-[[[(2,4-dioxo-1-imidazolidinyl)amino]carbonyl]amino]-2-thienylacetyl]amino]-8-oxo-5-thia-1-azabicyclo[4.2.0]-oct-2-ene-2-carboxylic acid, sodium salt The trifluoroacetic acid salt product from part (b) is treated with 1-[[(phenylthio)carbonyl]amino]-2,4-dioxoimidazolidine according to the procedure of Example 20 to yield 3-[(acetyloxy)methyl]-7α-methoxy-7β-[[DL-[[[(2,4-dioxo-1-imidazolidinyl)anino]carbonyl]amino]-2-thienylacetyl-]amino]-8-oxo-5-thia-1-azabicyclo[4.2.0-]oct-2-ene-2-carboxylic acid.

An equimolar solution of this compound and sodium bicarbonate is lyophilized to yield 3-[(acetyloxy)methyl- 7α-methoxy-7β-[[DL-[[[(2,4-dioxo-1-imidazolidinyl-)amino]-carbonyl]amino]-2-thienylacetyl]amino]-8-oxo-5-thia-1-azabicyclo[4.2.0]oct-2-ene-2-carboxylic acid,-sodium salt.

7α-Methoxy-7β-[[DL-[[[(2,4-dioxo-1-imidazolidinyl-)amino]-carbonyl]amino]-2-thienylacetyl]amino]-3-[[4-(aminocarbonyl)pyridinio]methyl]-[-oxo-5-thia-1-azabicyclo-[4.2.0]oct-2-ene-2-carboxylic acid An aqueous mixture of the sodium salt product of part (c), 4-pyridinecarboxamide, and potassium thiocyanate is reacted according to the procedure of Example 11 to yield 7α-methoxy-7β-[[DL-[[[(2,4-dioxo-1-imidazolidinyl)-amino]carbonyl]amino]-2-thienylacetyl]amino]-3-[[4-(aminocarbonyl)pyridinio]-methyl]-8-oxo-5-thia-1-azabicyclo[4.2.0]-oct-2-ene-2-carboxylic acid.

EXAMPLE 25

3-[(Acetyloxy)methyl]-7β-[[DL-[[[(2,4-dioxo-1-imidazolidinyl)-amino]carbonyl]amino]-2-thienylacetyl]amino]-8-oxo-5-thia-1-azabicyclo[4.2.0-]oct-2-ene-2-carboxylic acid By substituting DL-α-[[[(2,4-dioxo-1-imidazolidinyl)-amino]carbonyl]amino]-2-thiopheneacetic acid for the α-[[[(2,4-dioxo-1-imidazolidinyl)amino]carbonyl]-amino]benzeneacetic acid in the procedure of Example 7 and continuing as in Example 8, 3-[(acetyloxy)methyl]-7β-[[DL-[[[(2,4-dioxo-1-imidazolidinyl)amino]-carbonyl]amino]-2-thienylacetyl]amino]-8-oxo-5-thia-1-azabicyclo[4.2.0]oct-2-ene-2-carboxylic acid and sodium salt are obtained.

EXAMPLE 26

7β-[[(DL-[[[(2,4-dioxo-1-imidazolidinyl)amino]carbonyl]amino]-2-thienylacetyl]amino]-3-[[(1-oxo-2-pyridinyl)thio]methyl]-8-oxo-5-thia-1-azabicyclo[4.2.0-]oct-2-ene-2-carboxylic acid 0.003 mole of 3-[(acetyloxy)methyl]-7β-[[DL-[[[(2,4-dioxo-1-imidazolidinyl)amino]carbonyl]amino]-2-thienylacetyl]amino]-8-oxo-5-thia-1-azabicyclo[4.2.0-]oct-2-ene-2-carboxylic acid, sodium salt from Example 25 and 0.004 mole of 2-mercaptopyridine, 1-oxide, sodium salt are dissolved in 15 ml. of water and heated overnight at 50°. The reaction mixture is then diluted with water, filtered, and the clear solution is adjusted to pH 2 by the addition of 2N hydrochloric acid. The resulting precipitate is filtered under suction to obtain 7β-[[DL-[[[(2,4-dioxo-1-imidazolidinyl)amino]carbonyl]-amino]-2-thienylacetyl]amino]-3-[[(1-oxo-2-pyridinyl)thio]methyl]-8-oxo-5-thia-1-azabicyclo[4.2.0-]oct-2-ene-2-carboxylic acid.

Following the same procedure but employing 3-[-(acetyloxy)methyl]-7β-[[L-[[[(2,4-dioxo-1-imidazolidinyl)-amino]carbonyl]amino]-2-thienylacetyl]amino]-8-oxo-5-thia-1-azabicyclo[4.2.0-]oct-2-ene-2-carboxylic acid, sodium salt, there is obtained the corresponding final product in the L-form.

EXAMPLE 27

7β-[[D-[[[(2,4-dioxo-1-imidazolidinyl)amino]carbonyl]-amino]-2-thienylacetyl]amino]-3-[[(1-oxopyridazin-3-yl)thio]methyl]-8-oxo-5-thia-1-azabicyclo[4.2.0]oct-2-ene-2-carboxylic acid 3-[(Acetyloxy)methyl]-7β-[[D-[[[(2,4-dioxo-1-imidazolidinyl)amino]carbonyl]amino]-2-thienylacetyl]amino]-8-oxo-5-thia-1-azabicyclo[4.2.0-]oct-2-ene-2-carboxylic acid, sodium salt is dissolved in a mixture of acetone:water (1:1). 1-Oxopyridazine-3-thiol, sodium salt is added under nitrogen and the solution is heated for several hours at 60°. The solution is diluted with 150 ml. of water and acidified to pH 5 by the addition of 2N hydrochloric acid while cooling. A precipitate forms which is filtered under suction to yield 7β-[[D-[[[(2,4-dioxo-1-imidazolidinyl)amino]carbonyl]amino]-2-thienylacetyl]amino]-3-[[(1-oxopyridazin-3-yl)thio]methyl]-8-oxo-5-thia-1-azabicyclo[4.2.0]oct-2-ene-2-carboxylic acid.

EXAMPLES 28-36

Following the procedure of Example 27 but substituting for the 1-oxopyridazine-3-thiol one of the following:

2-oxopyridazine-3-thiol
6-methyl-1-oxopyridazine-3-thiol
6-methoxy-1-oxopyridazine-3-thiol
6-t-butyl-2-oxopyridazine-3-thiol
6-ethyl-2-oxopyridazine-3-thiol
6-hydroxy-1-oxopyridazine-3-thiol
6-hydroxy-2-oxopyridazine-3-thiol
6-chloro-1-oxopyridazine-3-thiol
6-chloro-2-oxopyridazine-3-thiol there is obtained, respectively:

7β-[[D-[[[(2,4-dioxo-1-imidazolidinyl)amino]carbonyl]-amino]-2-thienylacetyl]amino]-3-[[(2-oxopyridazin-3-yl)thio]-methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]-amino]-2-thienylacetyl]amino]-3-[[(6-methyl-1-oxopyridazin-3-yl)thio]methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]-amino]-2-thienylacetyl]amino]-3-[[(6-methoxy-1-oxopyridazin-3-yl)thio]methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]-amino]-2-thienylacetyl]amino]-3-[[(6-t-butyl-2-oxopyridazin-3-yl)thio]methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]amino]-2-thienylacetyl]amino]-3-[[(6-ethyl-2-oxopyridazin-3-yl)thio]methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]-amino]-2-thienylacetyl]amino]-3-[[(6-hydroxy-1-oxopyridazin-3-yl)thio]methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]-amino]-2-thienylacetyl]amino]-3-[[(6-hydroxy-2-oxopyridazin-3-yl)thio]methyl]-8-oxo-5-thia-1-azabicyclo[4.2.0 oct-2-ene-2-carboxylic acid;

7β-[[D-[[[(2,4-dioxo-1-imidazolidinyl)amino]carbonyl]-amino]-2-thienylacetyl]amino]-3-[[(6-chloro-1-oxopyridazin-3-yl)thio]methyl]-8-oxo-5-thia-1-azabicyclo[4.2.0]oct-2-ene-2-carboxylic acid;

7β-[[D-[[[(2,4-dioxo-1-imidazolidinyl)amino]carbonyl]-amino]-2-thienylacetyl]amino]-3-[[(6-chloro-2-oxopyridazine-3-yl)thio]methyl]-8-oxo-5-thia-1-azabicyclo[4.2.0]oct-2-ene-2-carboxylic acid, respectively.

Similarly, by substituting 3-[(acetyloxy)methyl]-7α-methoxy-7β-[[D-[[[(2,4-dioxo-1-imidazolidinyl)amino]carbonyl]-amino]-2-thienylacetyl]amino]-8-oxo-5-thia-1-azabicyclo[4.2.0]oct-2-ene-2-carboxylic acid, sodium salt for the 3-[(acetyloxy)methyl]-7β-[[D-[[[(2,4-dioxo-1-imidazolidinyl) amino]carbonyl]amino]-2-thienylacetyl]amino]-8-oxo-5-thia-1-azabicyclo[4.2.0]-oct-2-ene-2-carboxylic acid, sodium salt in the foregoing procedure and utilizing each of the named thiols, the corresponding final products having a 7α-methoxy group are obtained.

The following additional compounds are produced by the procedure of Examples 21 and 22. The 1-amino-2,4-dioxoimidazolidine of formula A below, having the substituents $R_2$ and $R_3$ in the table, is converted to the chlorocarbonylamino derivative of formula B as in Example 21, then this intermediate is made to react with the intermediate of formula C below, having the substituents R, $R_4$ and X in the table, as in Example 22 to obtain the product of formula D, having the substituents in the table.

| Example | A $R_2$ | A $R_3$ | B $R_3$ | C $R_4$ | C $R_3$ | C $R_2$ | R | D X |
|---|---|---|---|---|---|---|---|---|
| 37 | CH$_3$ | | H | thienyl | H | CH$_3$ | t-C$_4$H$_9$ | 1-methyl-5-methyl-tetrazol-2-yl-thio |
| 38 | H | | H | thienyl | H | H | -CH$_2$-C$_6$H$_5$ | 1-methyl-tetrazol-5-yl-thio |
| 39 | H | | H | 4-methylthienyl | H | H | -CH(C$_6$H$_5$)$_2$ | 1-ethyl-tetrazol-5-yl-thio |
| 40 | H | | H | 5-chlorothienyl | H | H | -CH$_2$CCl$_3$ | 1-methyl-tetrazol-5-yl-thio |
| 41 | C$_2$H$_5$ | | CH$_3$ | phenyl | CH$_3$ | C$_2$H$_5$ | -CH(C$_6$H$_5$)$_2$ | 1-methyl-tetrazol-5-yl-thio |
| 42 | H | | C$_2$H$_5$ | 4-hydroxyphenyl | C$_2$H$_5$ | H | -CH(C$_6$H$_5$)$_2$ | 1-methyl-tetrazol-5-yl-thio |

-continued
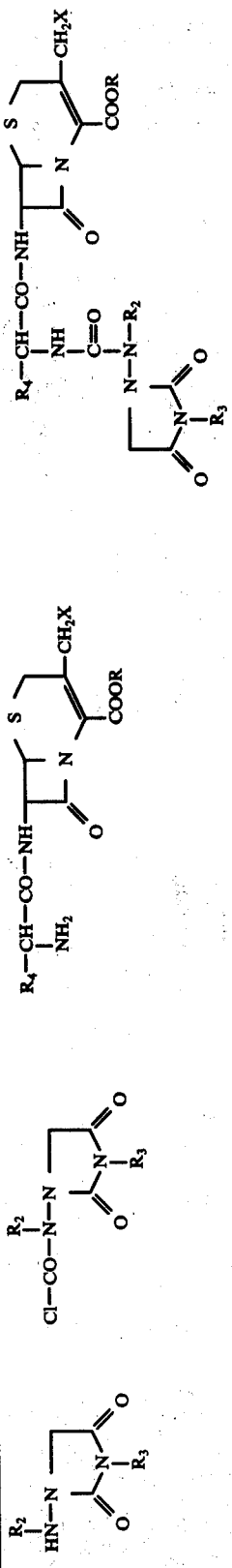
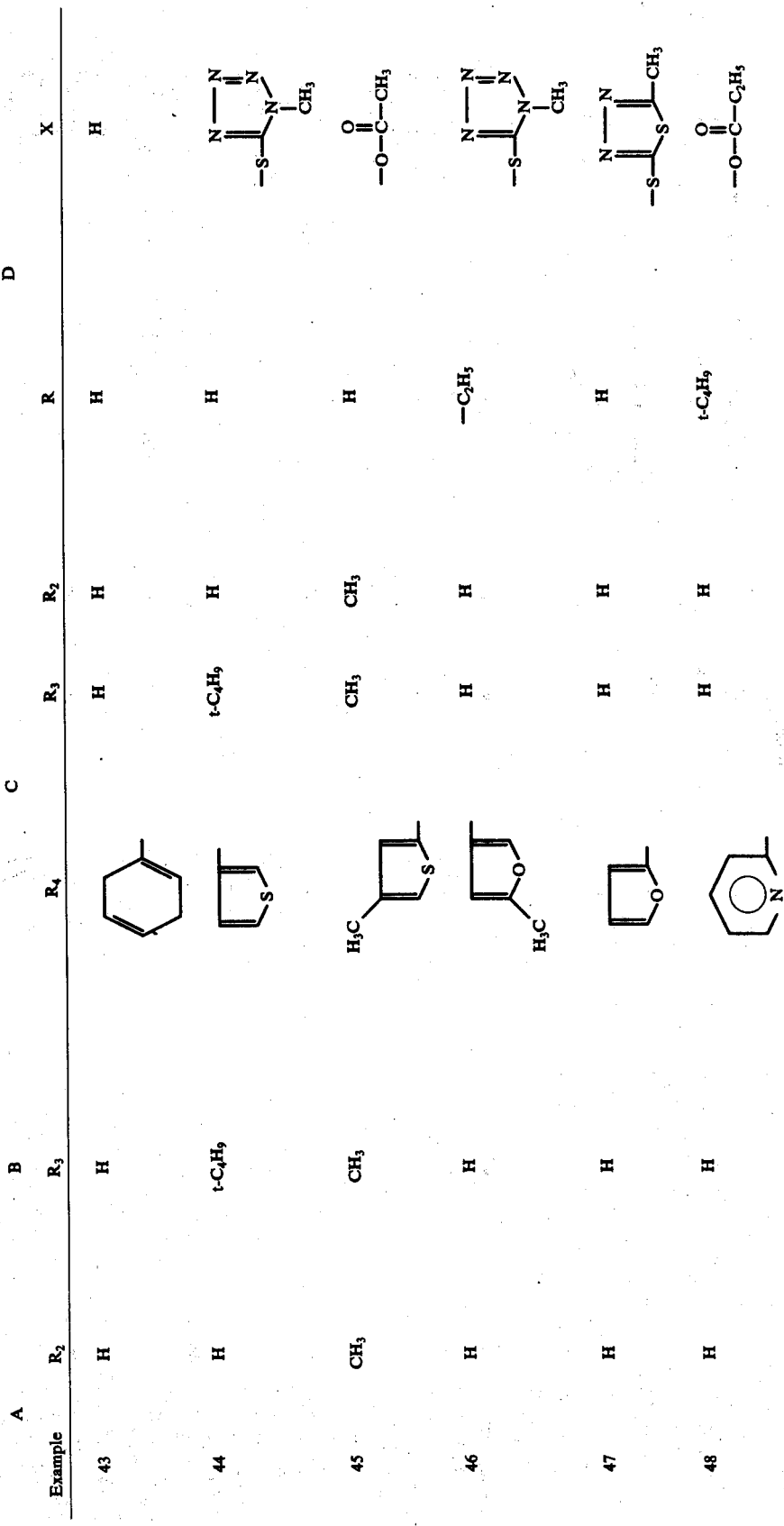
| Example | A R_2 | B R_3 | C R_4 | R_3 | R_2 | R | D X |
|---|---|---|---|---|---|---|---|
| 43 | H | H | (cyclohexenyl) | H | H | H | H |
| 44 | H | t-C_4H_9 | (thienyl) | t-C_4H_9 | H | H | (N-methyltetrazolylthio) |
| 45 | CH_3 | CH_3 | (methylthienyl) | CH_3 | CH_3 | H | -O-CO-CH_3 |
| 46 | H | H | (methylfuryl) | H | H | -C_2H_5 | (N-methyltetrazolylthio) |
| 47 | H | H | (dihydrofuryl) | H | H | H | (methylthiadiazolylthio) |
| 48 | H | H | (pyridyl) | H | H | t-C_4H_9 | -O-CO-C_2H_5 |

-continued

| Example | A R₂ | B R₃ | C R₄ | R₃ | R₂ | R | D X |
|---|---|---|---|---|---|---|---|
| 49 | H | H | 2-chloropyridin-yl | H | H | H | 1-methyl-tetrazol-5-yl-thio |
| 50 | H | H | pyridin-yl | H | H | H | 2-methyl-1,3,4-oxadiazol-5-yl-thio |
| 51 | CH₃ | H | H | H | CH₃ | —(CH₂)₂—C₆H₅ | 1,3,4-thiadiazol-2-yl-thio |
| 52 | H | H | cyclopentyl | H | H | H | 1,3-oxazolin-2-yl-thio |
| 53 | H | H | —C₂H₅ | H | H | t-C₄H₉ | —O—CO—CH₃ |
| 54 | H | CH₃ | cyclohexyl | CH₃ | H | —CH(C₆H₅)₂ | 1H-tetrazol-5-yl-thio |

-continued

| Example | A R₂ | A R₃ | B R₃ | C R₄ | C R₃ | C R₂ | R | D X |
|---|---|---|---|---|---|---|---|---|
| 55 | H | H | H | phenyl | H | H | -CH(C₆H₅)₂ | triazole-S- with N-C₂H₅ |
| 56 | H | H | H | phenyl | H | H | H | H |
| 57 | H | H | H | phenyl | H | H | H | triazole-S- with N-CH₃ |
| 58 | H | H | H | phenyl | H | H | -CH₂-C₆H₅ | -O-CO-CH₃ |
| 59 | C₄H₉ | H | H | phenyl | H | C₄H₉ | -CH(C₆H₅)(t-C₄H₉) | -O-CO-CH₃ |
| 60 | H | H | H | phenyl | H | H | H | triazole-S- with N-CH₃ |

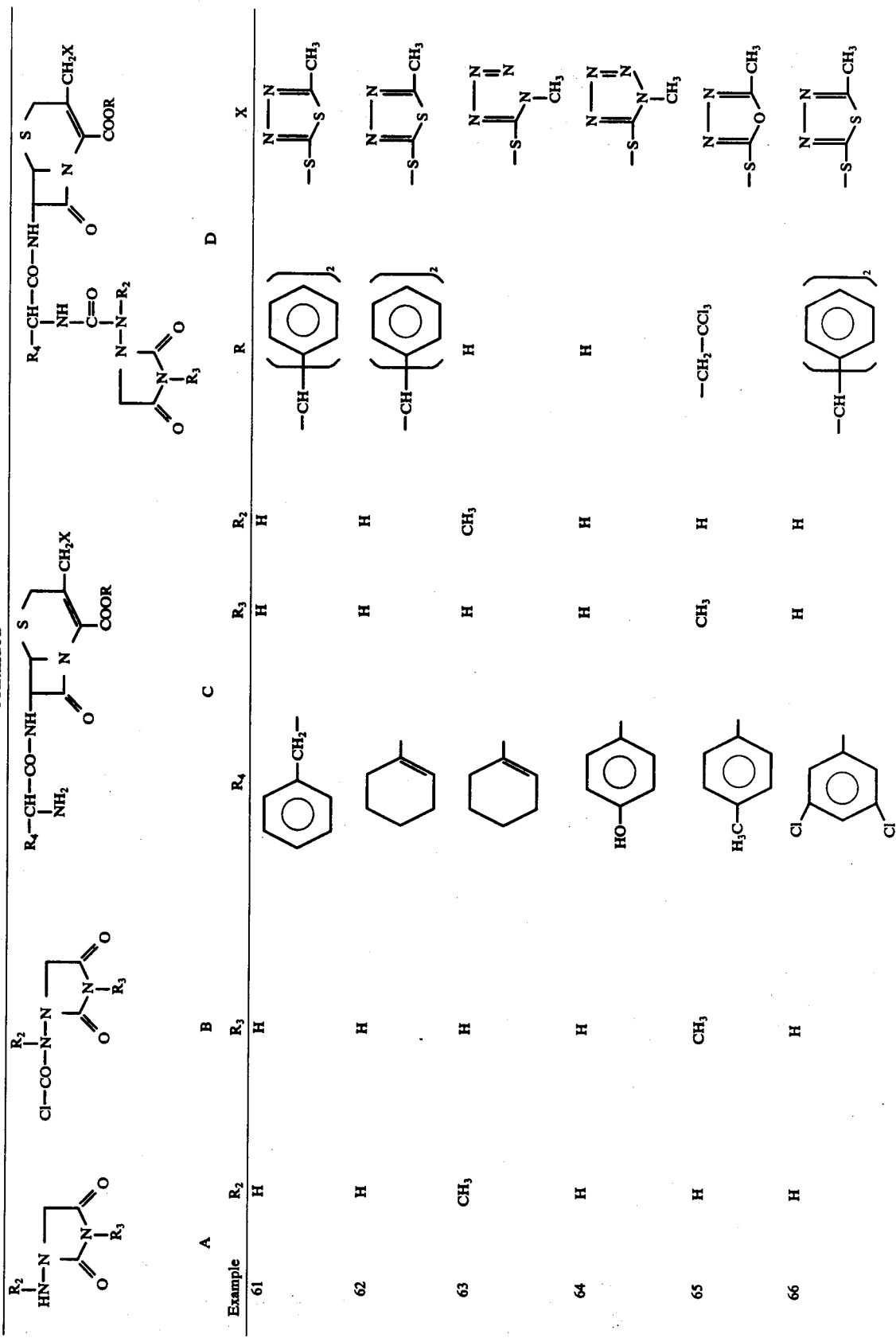

-continued

| | A | | | B | | C | | | D | |
|---|---|---|---|---|---|---|---|---|---|---|
| Example | $R_2$ | $R_3$ | | $R_3$ | $R_4$ | $R_3$ | $R_2$ | R | X |
| 67 | H | H | | H | 4-CH₃O-C₆H₄-CH₂- | H | H | t-C₄H₉ | 1-methyl-tetrazol-5-yl-S- |
| 68 | H | H | | H | thiophen-2-yl | H | H | H | 2-methyl-1,3,4-thiadiazol-5-yl-S- |
| 69 | H | H | | H | phenyl | H | H | -CH₂-C₆H₅ | 1,3,4-thiadiazol-2-yl-S- |
| 70 | H | H | | H | thiophen-2-yl | H | H | -CH(C₆H₅)₂ | 4-methyl-thiazol-2-yl-S- |
| 71 | H | H | | H | 4-HO-C₆H₄- | H | H | -CH(C₆H₅)₂ | 3-methyl-1,2,4-oxadiazol-5-yl-S- |
| 72 | H | H | | H | thiophen-2-yl | H | H | H | 1H-1,2,4-triazol-3-yl-S- |

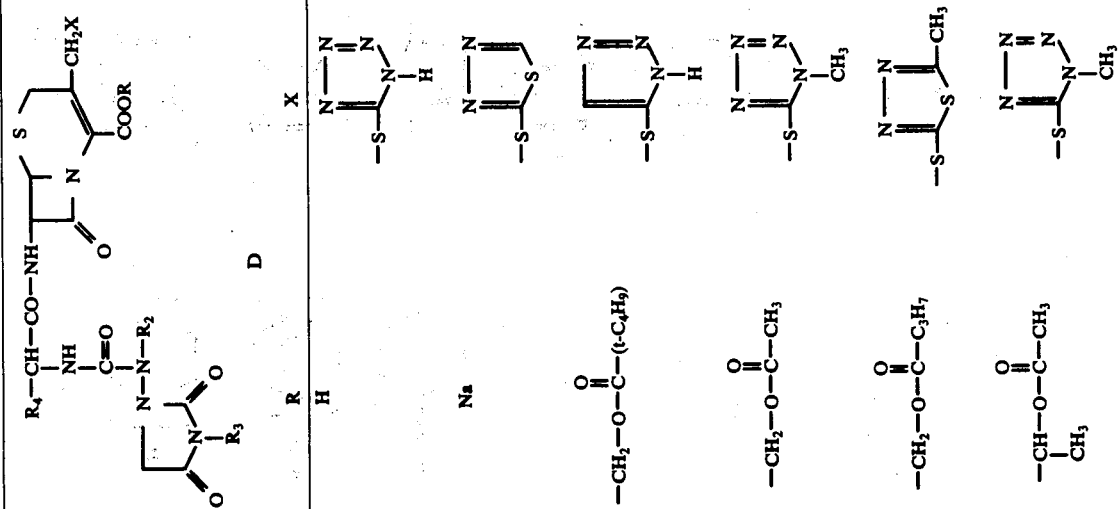
| Example | A R₂ | B R₃ | C R₄ | R₃ | R₂ | R | D X |
|---|---|---|---|---|---|---|---|
| 73 | H | H | 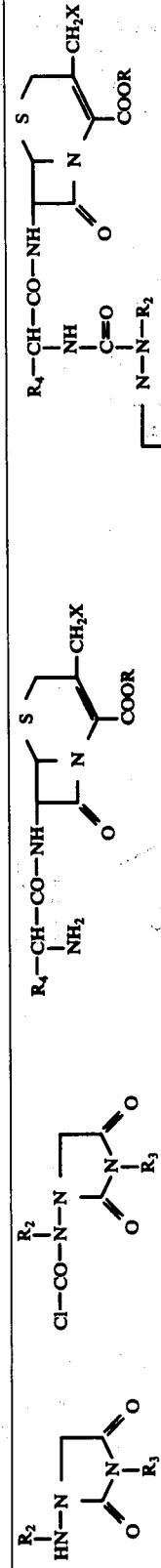 phenyl | H | H | H | N=N, N-H, S (tetrazole-SH) |
| 74 | H | H | thienyl | H | H | Na | N=N, S, S (thiadiazole) |
| 75 | H | H | phenyl | H | CH₃ | $-CH_2-O-\overset{O}{\underset{\|}{C}}-(t-C_4H_9)$ | N=N, N-H, S |
| 76 | H | H | thienyl | H | H | $-CH_2-O-\overset{O}{\underset{\|}{C}}-CH_3$ | N=N, N-CH₃, S |
| 77 | H | H | phenyl | H | H | $-CH_2-O-\overset{O}{\underset{\|}{C}}-C_3H_7$ | N=N, S-CH₃, S |
| 78 | H | H | thienyl | H | H | $-CH-O-\overset{O}{\underset{\|}{C}}-CH_3$, CH₃ | N=N, N-CH₃, S |

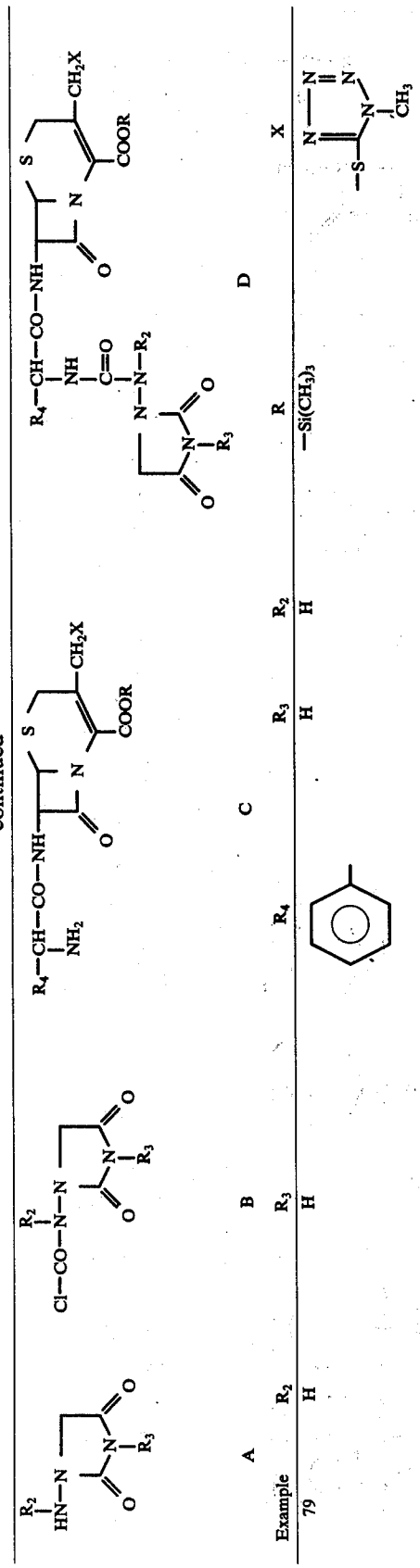

The following additional compounds are produced by the procedure of Examples 7 to 9. The acid of formula E below (derived as in Examples 5 and 6), having the substituents $R_2$, $R_3$ and $R_4$ in the table, is made to react with the 7-aminocephalosporanic acid derivative of formula F below as in either Example 7 or 9, then further treated as in either Example 8 or 10 to obtain the product of formula G.

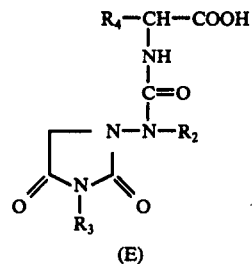
(E)

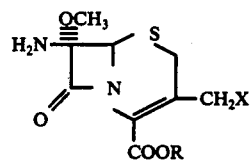
(F)

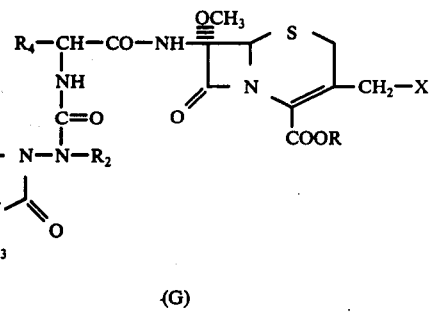
(G)

| Example | $R_2$ | $R_3$ | $R_4$ | R | X |
|---|---|---|---|---|---|
| 80 | H | H | 2-thienyl | t-$C_4H_9$ | -S-(5-methyl-1,3,4-thiadiazol-2-yl) |
| 81 | H | H | 2-thienyl | -$CH_2$-phenyl | -S-(1-methyl-1H-tetrazol-5-yl) |
| 82 | H | $CH_3$ | 2-thienyl | H | -S-(1-methyl-1H-tetrazol-5-yl) |
| 83 | H | H | 5-chloro-2-thienyl | -$CH_2CCl_3$ | -S-(1-ethyl-1H-tetrazol-5-yl) |
| 84 | H | H | 5-methyl-2-thienyl | -CH(phenyl)$_2$ | -O-CO-$CH_3$ |
| 85 | H | $C_2H_5$ | 2-thienyl | -CH(phenyl)$_2$ | -S-(1-methyl-1H-tetrazol-5-yl) |
| 86 | H | H | 2-thienyl | t-$C_4H_9$ | H |
| 87 | $C_2H_5$ | H | phenyl | -CH(phenyl)$_2$ | -S-(1-methyl-1H-tetrazol-5-yl) |
| 88 | H | H | 4-hydroxyphenyl | -CH(phenyl)$_2$ | -S-(1-methyl-1H-tetrazol-5-yl) |

-continued

| Example | R₂ | R₃ | R₄ | R | X |
|---|---|---|---|---|---|
| 89 | H | H | cyclohexenyl | —CH₂CCl₃ | —S-(1-methyl-tetrazol-5-yl) |
| 90 | H | H | cyclopentyl | —CH(C₆H₅)₂ | —O—C(=O)—CH₃ |
| 91 | H | H | 5-methyl-furan-2-yl | —C₂H₅ | —S-(1H-tetrazol-5-yl) |
| 92 | H | H | furan-2-yl | H | —S-(5-methyl-1,3,4-thiadiazol-2-yl) |
| 93 | H | H | pyridin-2-yl | t-C₄H₉ | —O—C(=O)—C₂H₅ |
| 94 | H | H | 2-chloropyridin-5-yl | —CH(C₆H₅)₂ | —S-(1-methyl-tetrazol-5-yl) |
| 95 | H | CH₃ | pyridin-4-yl | K | —S-(5-methyl-1,3,4-oxadiazol-2-yl) |
| 96 | H | H | H | —(CH₂)₂C₆H₅ | —S-(1,3,4-thiadiazol-2-yl) |
| 97 | H | H | —C₂H₅ | t-C₄H₉ | —O—C(=O)—CH₃ |
| 98 | H | H | cyclohexyl | —CH(C₆H₅)₂ | —S-(1H-tetrazol-5-yl) |
| 99 | H | H | cyclohexenyl | —CH(C₆H₅)₂ | —S-(1-ethyl-tetrazol-5-yl) |

-continued
(E)  (F)  (G)
| Example | R₂ | R₃ | R₄ | R | X |
|---|---|---|---|---|---|
| 100 | H | H | 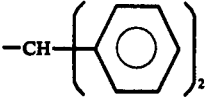 | $-CH(\text{C}_6\text{H}_5)_2$ | 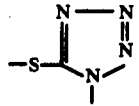 |
| 101 | H | H | 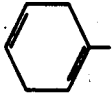 | $-CH_2\text{C}_6\text{H}_5$ | 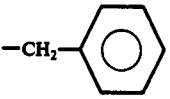 |
| 102 | H | H | 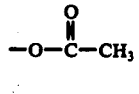 | $-CH(\text{C}_6\text{H}_5)_2$ | H |
| 103 | H | H | 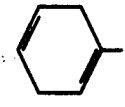 | H | H |
| 104 | H | H |  | t-C₄H₉ | 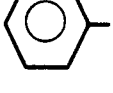 |
| 105 | CH₃ | H |  | $-CH(\text{C}_6\text{H}_5)_2$ | 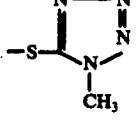 |
| 106 | H | H | 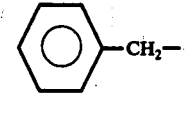 | $-CH(\text{C}_6\text{H}_5)_2$ |  |
| 107 | H | H | 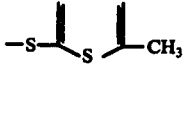 | $-CH_2-CCl_3$ |  |
| 108 | H | H |  | $-CH(\text{C}_6\text{H}_5)_2$ | 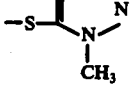 |
| 109 | H | H |  | t-C₄H₉ | 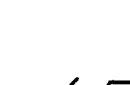 |

-continued

Structures (E), (F), and (G) shown above the table.

| Example | R₂ | R₃ | R₄ | R | X |
|---|---|---|---|---|---|
| 110 | H | H | 2-thienyl | $-CH(C_6H_5)_2$ | -S-C(=N)-S-CH=N (4-methyl-1,3-thiazol-2-ylthio) |
| 111 | H | H | phenyl | $-CH_2C_6H_5$ | 1,3,4-thiadiazol-2-ylthio |
| 112 | H | CH₃ | 2-thienyl | $-CH(C_6H_5)_2$ | 4-methyl-1,2-thiazol-5-ylthio |
| 113 | H | H | 4-hydroxyphenyl | H | 4-methyl-isoxazol-5-ylthio |
| 114 | CH₃ | CH₃ | 2-thienyl | $-CH(C_6H_5)_2$ | 1H-1,2,3-triazol-5-ylthio |
| 115 | H | H | phenyl | H | 1H-1,2,3-triazol-5-ylthio |
| 116 | H | H | 2-thienyl | $-CH_2-O-CO-CH_3$ | 1-methyl-1,2,3-triazol-5-ylthio |
| 117 | H | H | phenyl | $-CH_2-O-CO-C_3H_7$ | 5-methyl-1,3,4-thiadiazol-2-ylthio |
| 118 | H | H | 2-thienyl | $-CH(CH_3)-O-CO-CH_3$ | 1-methyl-1H-tetrazol-5-ylthio |
| 119 | H | H | phenyl | $Si(CH_3)_3$ | 1-methyl-1H-tetrazol-5-ylthio |

EXAMPLE 120

3-[(Acetyloxy)methyl]-7β-[[DL-[[[(2,4-dioxo-1-imidazolidinyl)-amino]carbonyl]amino]phenylacetyl]-amino]-8-oxo-5-thia-1-azabicyclo[4.2.0]oct-2-ene-2-carboxylic acid 2.72 g. (0.01 mol.) of 7-aminocephalosporanic acid are suspended in 30 ml. of anhydrous acetonitrile, 4.8 ml. of bis(trimethylsilyl)acetamide are added and the suspension is stirred until a clear solution results (solution A).

3.01 g. (0.01 mol.) of DL-α-[[[(2,4-dioxo-1-imidazolidinyl)amino]carbonyl]amino]benzeneacetic acid are added to 30 ml. of anhydrous acetonitrile and 1.35 g (0.01 mol.) of N-dimethylbenzylamine are added at room temperature. A viscous mass results which, on cooling, solidifies and divides. This is then added to 0.011 mol. of methyl chloroformate at −10°. The salt goes into solution with slight turbidity. To this solution A is added dropwise over a period of 10 minutes at −10°. The mixture becomes very turbid. This is stirred for 90 minutes whereupon the temperature slowly rises to 3°. 30 ml. of water are added, the mixture is stirred for 5 minutes and then 200 ml. of ethylacetate are added. By the addition of slightly dilute hydrochloric acid the pH is adjusted to 2. The layers are separated, the aqueous phase is extracted once with ethylacetate and the ethylacetate extracts are combined, then washed with water, dried with magnesium sulfate and concentrated in vacuum. The residue 3-[(acetyloxy)methyl]-7β-[[DL-[[[(2,4-dioxo-1-imidazolidinyl)amino]-carbonyl]amino]-phenylacetyl]amino]-8-oxo-5-thia-1-azabicyclo[4.2.0]oct-2-ene-2-carboxylic acid, is treated with ether and filtered under suction, yield 4.5 g., m.p. 152°–153° (dec).

EXAMPLE 121

D-α-[[[(2,4-dioxo-1-imidazolidinyl)amino]carbonyl]-amino]-2-thiopheneacetic acid 3.14 g. (0.02 mol.) of D-α-amino-2-thiophene acetic acid are suspended in 60 ml. of acetonitrile and 15.0 ml. of bis(trimethylsilyl)acetamide are added. The suspension is stirred until a clear solution of the trimethylsilyl ester results. 40.0 ml. of propylene oxide are added and then a solution of 3.55 g. (0.02 mol.) of 1-(chlorocarbonylamino)-2,4-dioxoimidazolidine in 80 ml. of anhydrous acetonitrile is added dropwise, then stirred at room temperature overnight. The solvent is evaporated in vacuum, water is added to the oily residue, neutralized with sodium bicarbonate and again concentrated. The solid residue is triturated with ether and filtered under suction. After drying, 10 ml. of 2N hydrochloric acid is added to the residue. After a short time, D-α-.[[[(2,4-dioxo-1-imidazolidinyl)amino]carbonyl]amino]-2-thiopheneacetic acid crystallizes, which is purified by recrystallization from water, yield, 3.2 g., m.p. 215° (dec).

b.
3-[(Acetyloxy)methyl]-7β-[[D-[[[(2,4-dioxo-1-imidazolidinyl)amino]carbonyl]amino]-2-thienylacetyl]amino]-8-oxo-5-thia-1-azabicyclo[4.2.0]-oct-2-ene-2-carboxylic acid The product of part (a) is reacted with 7-aminocephalosporanic acid according to the procedure of Example 22 to obtain 3-[(acetyloxy)methyl]-7β-[[D-[[[(2,4-dioxo-1-imidazolidinyl)amino]carbonyl]amino]-2-thienylacetyl]amino]-8-oxo-5-thia-1-azabicyclo[4.2.0]-oct-2-ene-2-carboxylic acid.

What is claimed is:

1. A compound of the formula

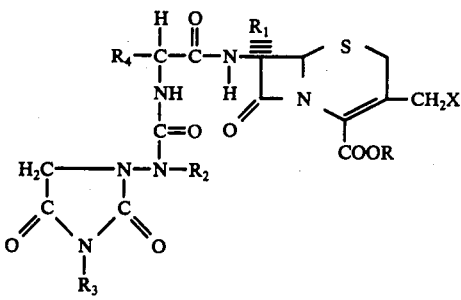

wherein R is hydrogen, lower alkyl, phenyl-lower alkyl, diphenyl-lower alkyl, tri(lower alkyl)silyl, trihaloethyl, aluminum, alkali metal, alkaline earth metal, phenyl-lower alkylamine, lower alkylamine, tri(lower alkyl)amine, N-lower alkylpiperidine or

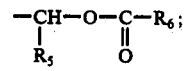

$R_1$ is in the α-configuration and is hydrogen or methoxy; $R_2$, $R_3$ and $R_5$ each is hydrogen or lower alkyl; $R_4$ is hydrogen, lower alkyl, cyclo-alkyl of 3 to 7 carbons, cycloalkenyl of 3 to 7 carbons, cycloalkadienyl of 6 or 7 carbons, phenyl, phenyl-lower alkyl, substituted phenyl or phenyl-lower alkyl wherein said phenyl substituent is one or two members selected from the group consisting of halogen, lower alkyl, lower alkoxy and hydroxy, or a mono substituted or unsubstituted heterocyclic selected from the group consisting of 2-thienyl, 3-thienyl, 2-furyl, 3-furyl, 2-pyridyl, 3-pyridyl and 4-pyridyl wherein said heterocyclic substituent is attached at an available carbon atom and is halogen or lower alkyl; $R_6$ is lower alkyl; and X is a heterothio group selected from the group consisting of

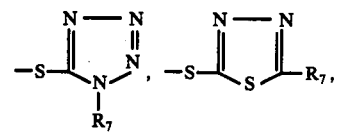

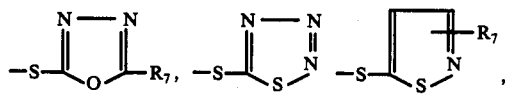

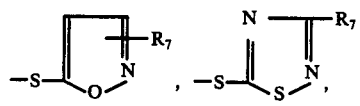

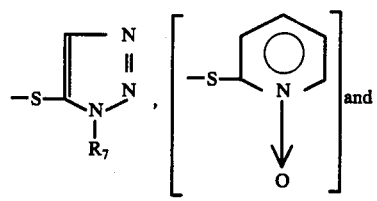

-continued

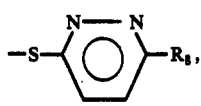

wherein $R_7$ is hydrogen or lower alkyl and $R_8$ is hydrogen, lower alkyl, methoxy, hydroxy or halogen.

2. A compound of claim 1 wherein R is hydrogen, alkali metal or diphenylmethyl; $R_1$ is hydrogen or methoxy; $R_2$ and $R_3$ each is hydrogen; $R_4$ is cyclohexadienyl, phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a mono substituted or unsubstituted heterocyclic selected from the group consisting of 2-thienyl, 3-thienyl, 2-furyl, 3-furyl, 2-pyridyl, 3-pyridyl, and 4-pyridyl wherein said heterocyclic substituent is attached at an available carbon atom and is chloro, bromo, methyl, or ethyl; and X is 1-methyltetrazolylthio or 5-methyl-1,3,4-thiadiazolylthio.

3. A compound of claim 1 wherein $R_4$ is phenyl.

4. A compound of claim 1 wherein $R_4$ is thienyl.

5. A compound of claim 1 wherein $R_2$ and $R_3$ each is hydrogen.

6. A compound of claim 1 wherein X is (1-methyl-1H-tetrazol-5-yl)thio.

7. The compound of claim 1 wherein $R_4$ is phenyl, R, $R_1$, $R_2$ and $R_3$ each is hydrogen and X is (1-methyl-1H-tetrazol-5-yl)thio.

8. The compound of claim 1 wherein $R_4$ is 2-thienyl; R, $R_1$, $R_2$ and $R_3$ each is hydrogen and X is (1-methyl-1H-tetrazol-5-yl)thio.

9. The compound of claim 1 wherein $R_4$ is phenyl, R is sodium, $R_1$, $R_2$ and $R_3$ each is hydrogen and X is (1-methyl-1H-tetrazol-5-yl)thio.

10. The compound of claim 1 wherein $R_4$ is 2-thienyl, R is sodium, $R_1$, $R_2$ and $R_3$ each is hydrogen and X is (1-methyl-1H-tetrazol-5-yl)thio.

11. The D-form of the compound of claim 10.

12. A compound of claim 1 wherein X is

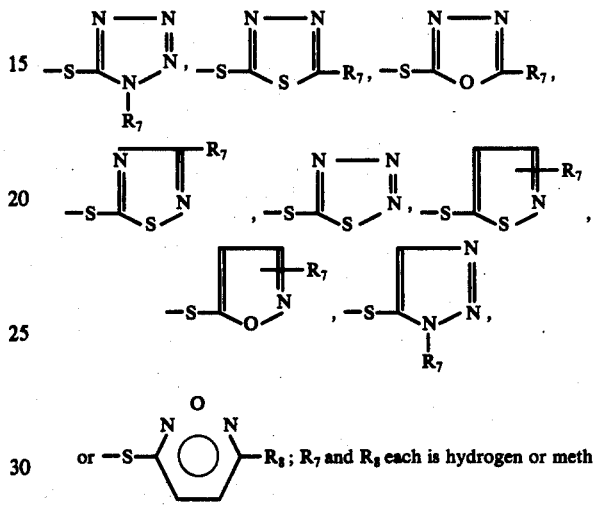

$R_7$ and $R_8$ each is hydrogen or methyl.

* * * * *